United States Patent
Yamane (10) Patent No.: US 8,974,377 B2
(45) Date of Patent: Mar. 10, 2015

(54) ENDOSCOPE FORCEPS PLUG (71) Applicant: FUJIFILM Corporation, Tokyo (JP)

(72) Inventor: Kenji Yamane, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 57 days.

(21) Appl. No.: 13/624,617

(22) Filed: Sep. 21, 2012

(65) Prior Publication Data

US 2013/0085327 A1 Apr. 4, 2013

(30) Foreign Application Priority Data

Sep. 30, 2011 (JP) ................... 2011-216684

(51) Int. Cl.
*A61B 1/00* (2006.01)
*A61B 1/04* (2006.01)

(52) U.S. Cl.
CPC ................... *A61B 1/00137* (2013.01)
USPC .......................... 600/154; 600/153

(58) Field of Classification Search
CPC ........... A61B 1/00137; A61B 1/00059; A61B 1/0052; A61B 1/018
USPC ................ 600/154, 104, 114, 153; 604/167.01–167.06; 348/45; 356/241.1
See application file for complete search history.

(56) References Cited

U.S. PATENT DOCUMENTS 4,920,953 A * 5/1990 McGown ................ 600/154

FOREIGN PATENT DOCUMENTS

JP 2009-183432 A 8/2009
JP 2009-268777 A 11/2009

* cited by examiner

*Primary Examiner* — Anhtuan T Nguyen
*Assistant Examiner* — Timothy J Neal
(74) *Attorney, Agent, or Firm* — Birch, Stewart, Kolasch & Birch, LLP (57) ABSTRACT

A main body that has an installation portion which is formed from an elastic material having a cylinder shape, and installed at the metal opening at one end side; a lid insertion portion which cylindrically protrudes to the other end side, and a lid connected to the main body by a flexible connection portion having flexibility, that is formed from an elastic material, that has a tube shape with a cylindrical insertion channel, and that, at both sides where both ends of the insertion channel are respectively open, has first and second installation portions with different external shapes to each other which are installed by selectively inserting to the lid insertion portion. The first installation portion has a larger external shape than the second installation portion, at least a portion of a diameter of the insertion channel decreases when installed to the lid insertion portion of the first installation portion.

12 Claims, 10 Drawing Sheets

ENDOSCOPE FORCEPS PLUG

BACKGROUND OF THE INVENTION

1. Field of the Invention

The present invention relates to an endoscope forceps plug which is used by being installed at a metal opening provided at an inlet port thereof when inserting a treatment instrument to a treatment instrument insertion channel of an endoscope.

2. Description of the Related Art

In the related art, a medical endoscope may not only observe a state inside a body, but may also collect a tissue cell thereof and perform a predetermined treatment when a lesion or the like is present inside the body. For that reason, the endoscope has a treatment instrument insertion channel where the forceps or the other treatment instruments are inserted to an insertion part thereof. The proximal end of the treatment instrument insertion channel leads to a treatment instrument guide section which is provided at a main body operation section and in addition, a distal end is open as a treatment instrument outlet port together with an observation section or the like which is provided at a distal end surface or a distal end side surface of the insertion part.

A forceps plug (stopcock body) is attached to the treatment instrument guide section via the metal opening. The forceps plug stops up the treatment instrument guide section so that blood, waste inside the body, saline for internal lavage and the like which flow backward from inside the body of a subject may not leak outward from the treatment instrument guide section.

In order to meet demand for diversified or complicated surgeries using the endoscope, the endoscope forceps plug which is effective with respect to various treatment instruments is needed. In the present circumstances, the forceps plug includes an insertion channel for a valve into which the treatment instrument is inserted so as to prevent liquid leakage when using the treatment instrument. However, the many different sizes of treatment instrument cause difficulties in managing both the liquid leakage prevention and a reasonable insertion resistance to the treatment instrument. When using a large-sized treatment instrument, the insertion resistance increases and the endoscope is adversely affected.

For example, an endoscope forceps plug disclosed in JP2009-268777A integrally includes a cylindrical main body section that is fixed to a forceps entrance which is an inlet port of a treatment instrument insertion channel and where an insertion channel for admitting a treatment instrument is formed, a stopcock that is detachably attached to the upper part of the main body via a connection section, and a stopper member that is formed in a shape of a columnar block at the main body via the connection section of a band-like body. The stopper member has a notched portion oriented from the outer periphery to the center and fixes the treatment instrument in such a manner that the notched portion pinches the treatment instrument which is admitted to the insertion channel of the main body. The stopper member may be used in combination with the stopcock. Since the stopper member having the notched portion is integrally provided at the forceps plug main body, the forceps entrance section may not be substantially changed, a simple configuration allows the treatment instrument to be fixed and the treatment instrument may be easily fixed at a desired insertion place.

In addition, an endoscope forceps plug disclosed in JP2009-183432A is configured from a main body which has an insertion channel and a cylindrical elastic tube body that has at least one closed distal end which is fitted to the insertion channel. The elastic tube body has a longer length than a main body insertion channel, an outer diameter which is approximately the same as or slightly larger than an inner diameter of the insertion channel, and is closely placed while maintaining an urging force which spreads in the radial direction from the center with respect to the insertion channel. As a result, a highly sealed state is maintained inside a treatment instrument insertion channel or inside a suction tube which communicates with the channel. Thus, air or fluid inside a subject is prevented from leaking or flowing out from a distal end through the treatment instrument insertion channel. The influence of being worn out or a decrease in restoring force due to repeated uses may be reduced. In addition, the elastic tube body may be deformed such that a side surface thereof is crushed when inserting the treatment instrument and thereby may allow the treatment instrument to pass through.

SUMMARY OF THE INVENTION

However, endoscope forceps plugs in JP2009-268777A and JP2009-183432A are not disclosed or suggested to be effective with respect to various treatment instruments. For that reason, when a plurality of treatment instruments is required for a series of surgery, with respect to the treatment instruments other than a treatment instrument which has a certain diameter, problems will occur in that both a smooth insertion of the treatment instrument and a complete prevention of scattering contaminated liquid or the like are insufficient.

The present invention has been made in view of the above-mentioned problems and an object of the present invention is to provide an endoscope forceps plug that may properly use plural kinds of treatment instruments, may prevent liquid leakage during a treatment instrument insertion and may have an excellent insertion performance.

In order to achieve the above described object, according to the present invention, there is provided an endoscope forceps plug that is used by being installed at a metal opening which communicates with an insertion channel provided at an endoscope so as to insert a treatment instrument, and includes a main body that has an installation portion which is formed of an elastic material, having a cylinder shape and installed at the metal opening at one end side, and a lid insertion portion which cylindrically protrudes to the other end side, and, a lid that is connected to the main body by a flexible connection portion having flexibility, that is formed of an elastic material, that has a tube shape with a cylindrical insertion channel inside into which the treatment instrument is inserted, and that, at both sides where both ends of the insertion channel are respectively open, has first and second installation portions with different external shapes to each other which are installed by being selectively inserted to the lid insertion portion. The first installation portion has a larger external shape than the second installation portion, at least a portion of a diameter of the insertion channel decreases in a case of installing the first installation portion to the lid insertion portion, and the diameter of the insertion channel is unchanged in a case of installing the second installation portion to the lid insertion portion. In addition, the main body may have a slit at a center portion and the center portion of the main body is closed by a normally closed pit membrane which is open in a state of inserting the treatment instrument.

The first installation portion may include a first insertion portion which is inserted to a back side of the lid insertion portion, at a front part in an insertion direction to the lid insertion portion, and the second installation portion may include a second insertion portion which is inserted to the back side of the lid insertion portion, at the front part in the insertion direction to the lid insertion portion. In addition, the first installation portion may include a first fitting portion which is fitted to an upper part of the lid insertion portion, at a rear part in the insertion direction to the lid insertion portion, and the second installation portion may include a second fitting portion which is fitted to the upper part of the lid insertion portion, at the rear part in the insertion direction to the lid insertion portion.

Here, the first fitting portion may have a larger outer diameter than the second fitting portion, in a state where the first and second insertion portions have the same outer diameter. In addition, the first insertion portion has a larger outer diameter than the second insertion portion, in a state where the first and second fitting portions have the same outer diameter. Furthermore, the first insertion portion may have a larger outer diameter than the second insertion portion and the first fitting portion may have a larger outer diameter than the second fitting portion, in a state where the first and second insertion portions have different outer diameters and the first and the second fitting portions have different outer diameters.

The installation portion of the main body may have an elastic protrusion that protrudes on an inner peripheral surface and the elastic protrusion is detachably fitted into a forceps plug attachment groove which is formed on an outer peripheral surface of the metal opening. In addition, indications corresponding to inner diameters of insertion channels formed at the corresponding lids may be provided at the respective connection portions.

According to a configuration of the present invention, in response to an insertion direction of the lid, a portion of the treatment instrument insertion channel becomes slender (diameter of a portion of the treatment instrument insertion channel becomes small) or is changed in one side attachment direction and the portion of the treatment instrument insertion channel does not become slender or is not changed in the other side attachment direction. Therefore, liquid leakage may be prevented and a state of good insertion performance may also be realized.

According to the endoscope forceps plug of the present invention, when inserting the treatment instrument, liquid leakage may be prevented and a state of good insertion performance may also be realized.

DESCRIPTION OF THE PREFERRED EMBODIMENTS

Herein, preferred embodiments of the present invention will be described in detail with reference to the accompanying drawings. Furthermore, in the description and the drawings, configuration elements which have substantially the same function are omitted in repeated descriptions by designating the same reference numeral.

Figure 1:
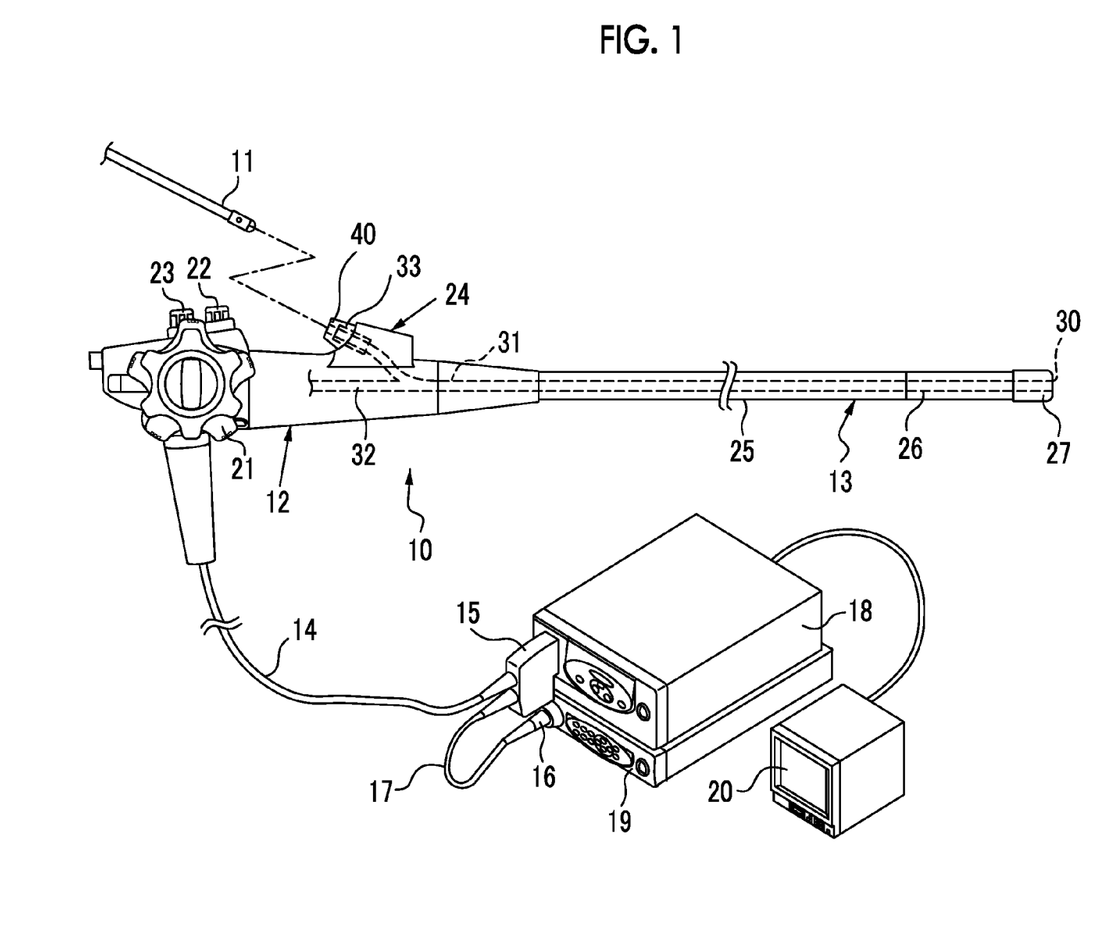
FIG. 1 is a perspective view including a partial front view illustrating a schematic configuration of an endoscope system.

Referring to FIG. 1, an endoscope 10 includes an operation section 12, an insertion section 13 and a universal cord 14. The universal cord 14 is connected to a light source device 18 and a processor 19 through connectors 15 and 16 and a cable 17.

The operation section 12 has an angle knob 21, an air and water supply button 22, and a suction button 23. The operation section 12 has a treatment instrument guide section 24 at the insertion section 13 side. Various treatment instruments 11 are inserted from the treatment instrument guide section 24.

The insertion section 13 is connected to the operation section 12 and inserted to inside a body of a subject. The insertion section 13 includes a flexible portion 25 which has flexibility, a bending portion 26 which is freely bendable and a rigid distal end 27, sequentially from the operation section 12 side thereof. The flexible portion 25 has a length to allow the rigid distal end 27 to reach an objective position inside the body. The bending portion 26 is interlocked by an operation of the angle knob 21 of the operation section 12 to move and bend in upward, downward, left and right direction, and directs the rigid distal end 27 to a desired direction inside the body.

The rigid distal end 27, on the distal end surface, has a treatment instrument outlet 30 in addition to an observation window, an illumination window, an air and water supply nozzle (all not illustrated). At an inner part of the observation window, an imaging unit such as objective optical systems, CCD or CMOS image sensors are arranged. An imaging signal from the imaging unit is transmitted to the processor 19 through the universal cord 14 or the like. The processor 19 performs various imaging processes with respect to the imaging signal of the imaging unit to convert to a video signal, which is displayed on a monitor 20 as an observation image.

The illumination window has a light exiting end of a light guide. The light guide guides an illumination light from an irradiation light source of the light source device 18 to the illumination window. The illumination light from the illumination window is irradiated toward an observation spot inside the body. The air and water supply nozzle injects air or water supplied from an air and water supply device (not illustrated) toward the observation window in response to an operation of the air and water supply button 22.

The treatment instrument outlet 30 is connected to a treatment instrument insertion channel 31 arranged inside the insertion section 13 and communicated with the treatment instrument guide section 24. The treatment instrument insertion channel 31 has a suction channel 32 which is divided near the treatment instrument guide section 24. The suction channel 32 is connected to the suction button 23. The suction button 23 is connected to a suction pump (illustration omitted) through the universal cord 14. The suction pump is usually driven during the operation of the endoscope 10. Accordingly, by the pressing operation of the suction button 23, blood, body fluids, waste, rinse water or the like inside the body is sucked from the suction channel 32 and the treatment instrument insertion channel 31. The treatment instrument guide section 24 has a fixed metal opening 33. The metal opening 33 is made of metal and cylindrically formed.

Figure 2:
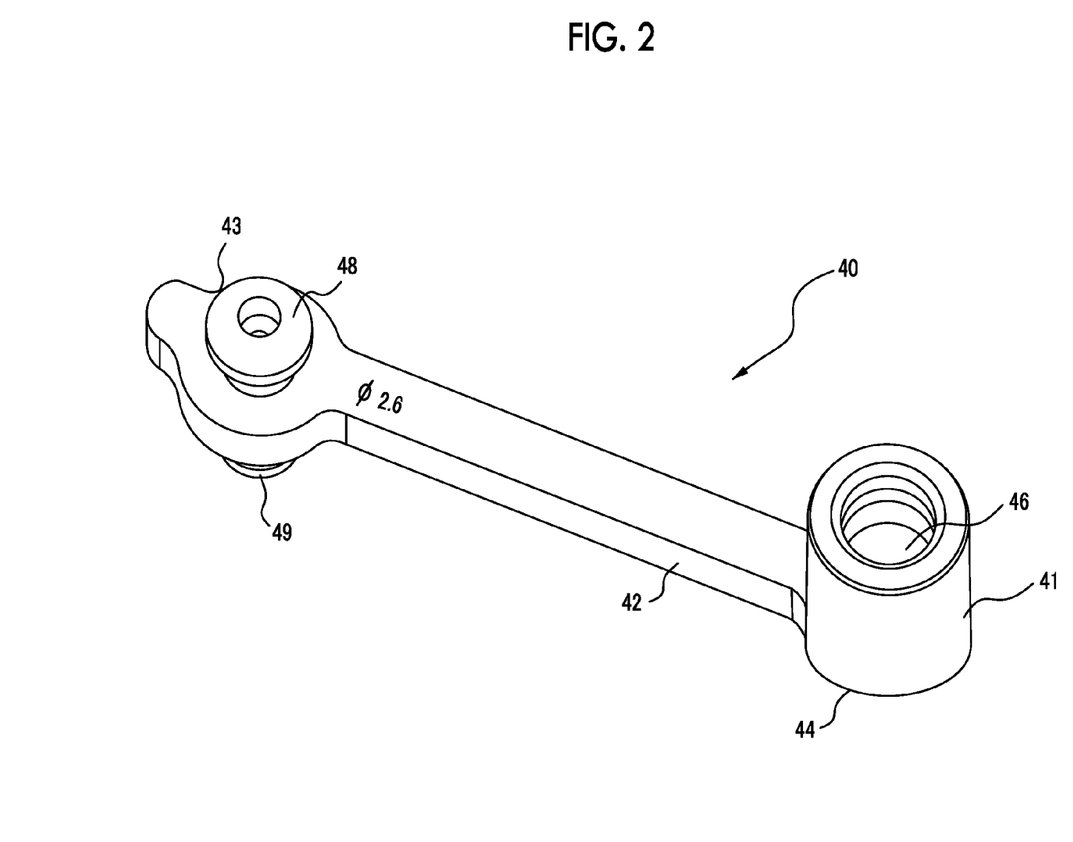
FIG. 2 is an outline view of an endoscope forceps plug according to an embodiment of the present invention.
Figure 3A:
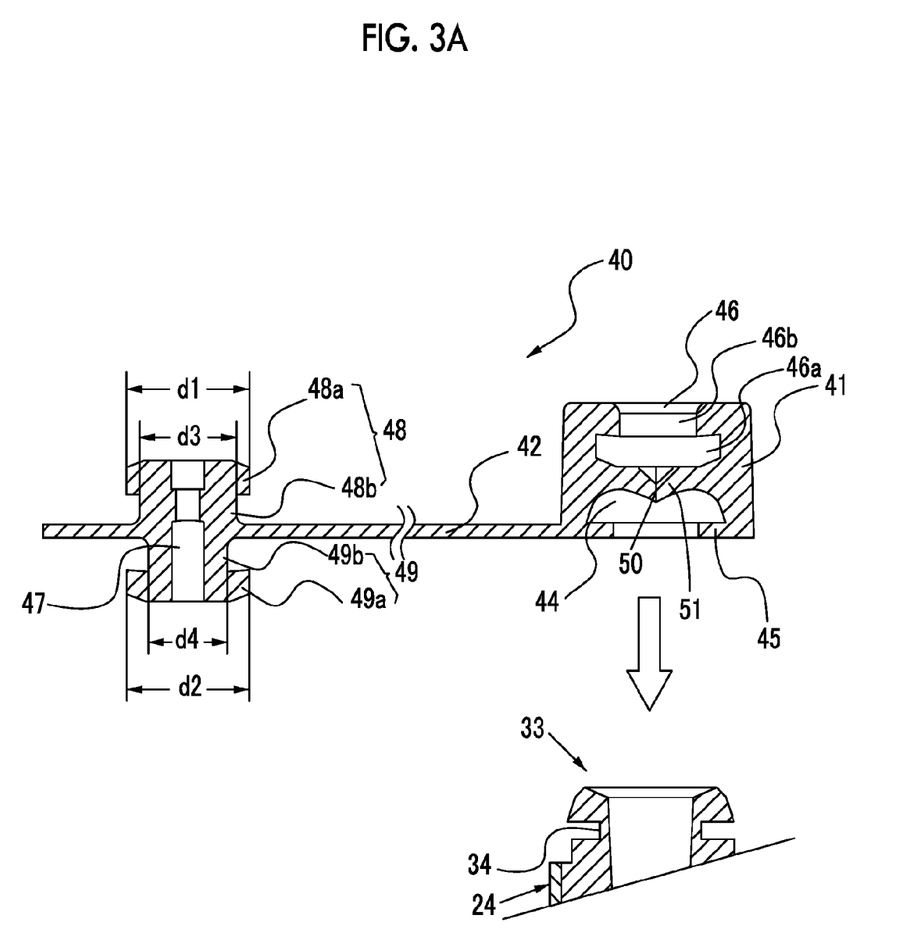
FIG. 3A is a cross-sectional view of an endoscope forceps plug according to an embodiment.
Figure 3B:
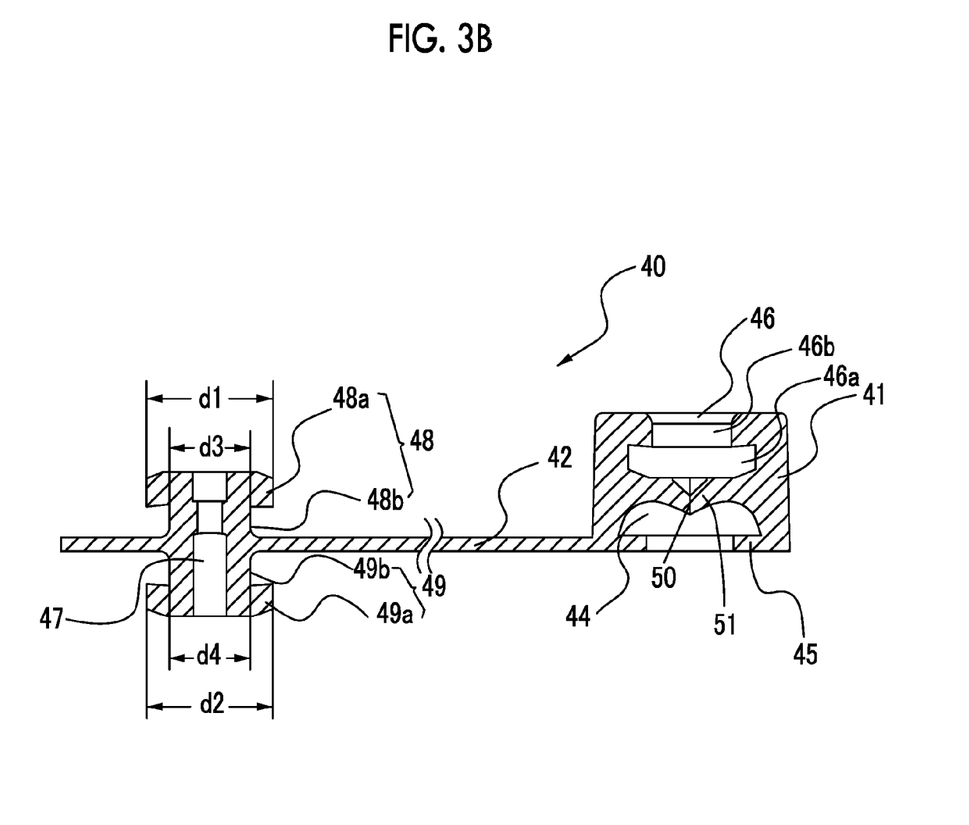
FIG. 3B is a cross-sectional view of an endoscope forceps plug according to an embodiment.
Figure 3C:
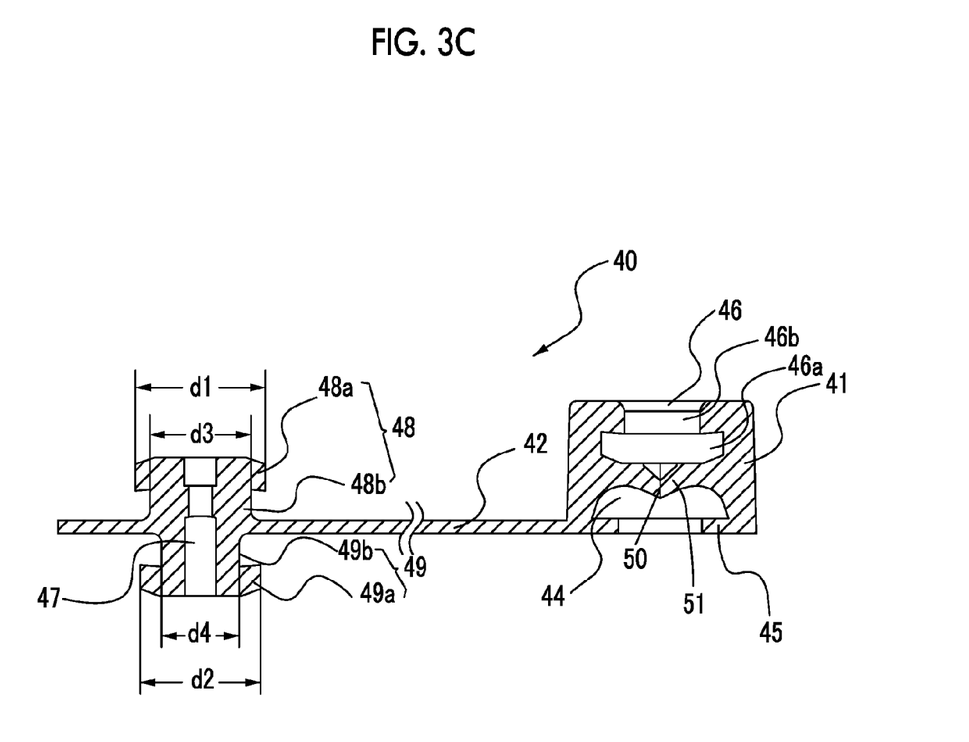
FIG. 3C is a cross-sectional view of an endoscope forceps plug according to an embodiment.

FIGS. 2, 3A to 3C illustrate a configuration of an endoscope forceps plug 40 according to an embodiment of the present invention. As illustrated in FIG. 2, the endoscope forceps plug 40 is integrally molded from a main body 41, a band-like portion 42 as the connection portion and a lid 43 using an elastic material. The main body 41 is tube-shaped and at one end, has an installation portion 44 which is installed at the metal opening 33. To be exact, as illustrated in FIGS. 3A to 3C, in the concave installation portion 44, an elastic protrusion 45 which protrudes on an inner peripheral surface of the installation portion 44 is detachably fitted to a forceps plug attachment groove 34 which is formed on an outer peripheral surface of the metal opening 33 and may be disengaged from the forceps plug attachment groove 34 by elastically deforming the periphery of the elastic protrusion 45. In addition, a concave lid insertion portion 46 which cylindrically protrudes to the other end side of the main body 41 is provided.

The lid 43 is tube-shaped, connected to the main body 41 by the flexible band-like portion 42 which has flexibility, and inside, has a cylindrical insertion channel 47 into which the treatment instrument is inserted. Both ends of the insertion channel 47 are respectively open and both end portions have a first insertion portion 48a and a second insertion portion 49a which are installable by being selectively inserted to a back side 46a of the lid insertion portion 46 of the main body 41. At a base of the first insertion portion 48a and the second insertion portion 49a, a first fitting portion 48b and a second fitting portion 49b which are fitted to an upper part 46b of the lid insertion portion 46 are respectively provided. Hereinafter, the first insertion portion 48a and the first fitting portion 48b are together referred to as a first installation portion 48. However, in a state where the first installation portion 48 is installed, the external shape of the first installation portion 48 is larger than a hole shape of the lid insertion portion 46 of the main body 41 such that an inner diameter of the first fitting portion 48b is elastically deformed. In addition, the second insertion portion 49a and the second fitting portion 49b are together referred to as a second installation portion 49. The external shapes of the first installation portion 48 and the second installation portion 49 are slightly larger than the hole shape of the lid insertion portion 46 such that the first installation portion 48 and the second installation portion 49 are elastically deformed and installed to the lid insertion portion 46.

Herein, as illustrated in FIG. 3A, the outer diameter d3 of the first fitting portion 48b is larger than the outer diameter d4 of the second fitting portion 49b, when outer diameters d1 and d2 of the first insertion portion 48a and the second insertion portion 49a are the same. In addition, as illustrated in FIG. 3B, the outer diameter d1 of the first insertion portion 48a is larger than the outer diameter d2 of the second insertion portion 49a, when the outer diameter d3 of the first fitting portion 48b is the same as the outer diameter d4 of the second fitting portion 49b. In addition, as illustrated in FIG. 3C, when the outer diameter d1 of the first insertion portion 48a is different from the outer diameter d2 of the second insertion portion 49a and the outer diameter d3 of the first fitting portion 48b is different from the outer diameter d4 of the second fitting portion 49b, the outer diameter d1 of the first insertion portion 48a is larger than the outer diameter d2 of the second insertion portion 49a and the outer diameter d3 of the first fitting portion 48b is larger than the outer diameter d4 of the second fitting portion 49b. Furthermore, the main body 41 of the forceps plug 40, at a center portion, has a linear slit 50 to which the treatment instrument is admitted and the center portion of the main body 41 is closed by a normally closed pit membrane 51 which is open when inserting the treatment instrument.

Figure 4A:
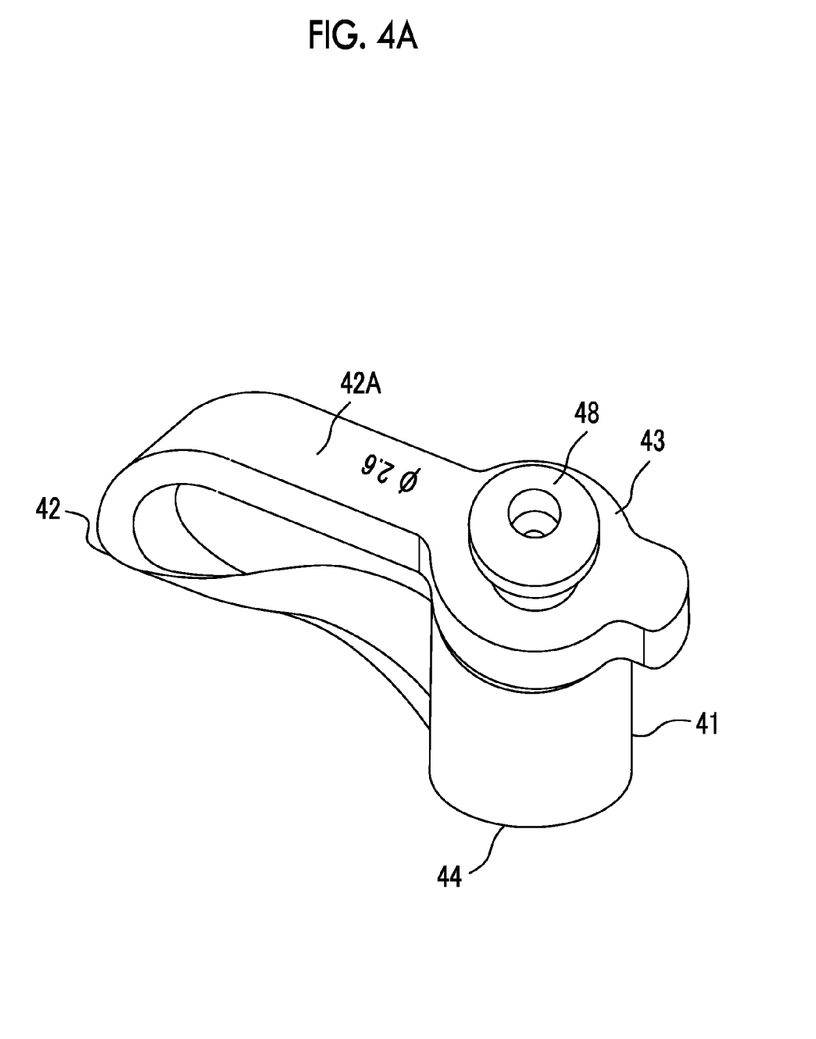
FIG. 4A is an outline view of a forceps plug when installing a second installation portion at a lid insertion portion.
Figure 4B:
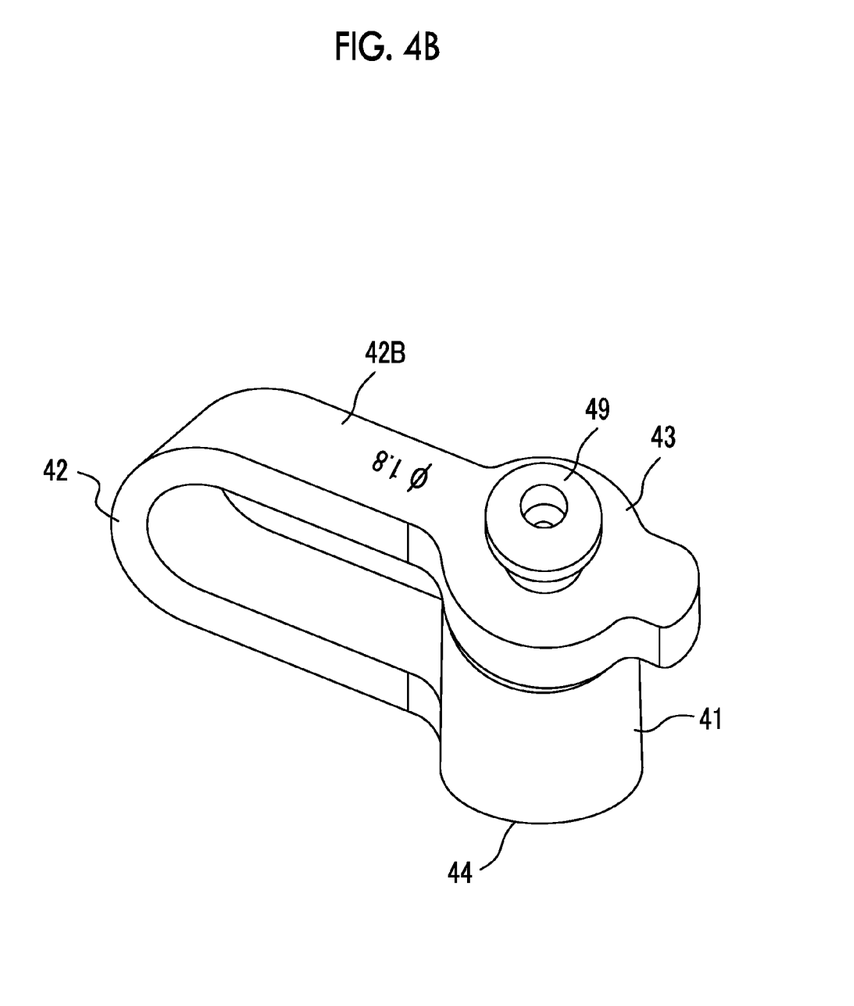
FIG. 4B is an outline view of a forceps plug when installing a first installation portion at a lid insertion portion.

As illustrated in FIGS. 4A and 4B, a band-like portion 42A of the first insertion portion 48a side of the lid 43 and a band-like portion 42B of the second insertion portion 49a side of the lid 43 have indications corresponding to inner diameters of different insertion channels. It is indicated on the band-like portion 42A that the of the insertion portion of the treatment instrument which is inserted has a 2.6 mm outer diameter. It is indicated on the band-like portion 42B that the insertion portion of the treatment instrument which is inserted has a 1.8 mm outer diameter.

Figure 5:
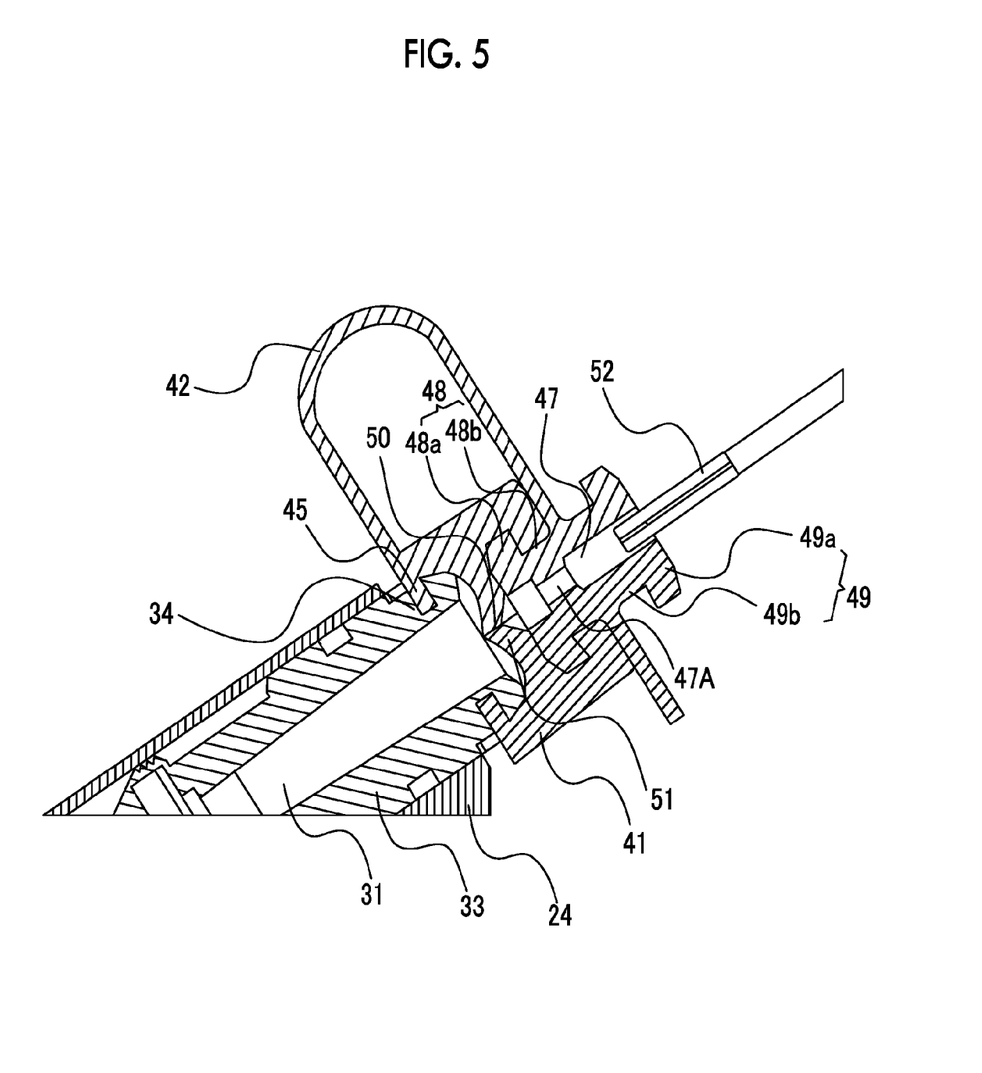
FIG. 5 is a cross-sectional view of a forceps plug when installing a first installation portion at a lid insertion portion.

FIG. 5 is a cross-sectional view of the forceps plug 40 when installing the first installation portion 48 of the lid 43 at the lid insertion portion 46 of the main body 41. When the first installation portion 48 of the lid 43 is installed at the lid insertion portion 46 of the main body 41, the outer diameter d3 of the first fitting portion 48b is large, the outer diameter d1 of the first insertion portion 48a is large, or both of the outer diameter d3 of the first fitting portion 48b and the outer diameter d1 of the first insertion portion 48a are large. Accordingly, the first installation portion 48 is pressed by the outside of the main body 41 and the insertion channel 47A inside the first installation portion 48 becomes slender than before the first installation portion 48 is installed at the lid insertion portion 46. That is, the diameter of the insertion channel 47A becomes small. The treatment instrument 52 is inserted to the insertion channel 47 of the lid 43.

Figure 6:
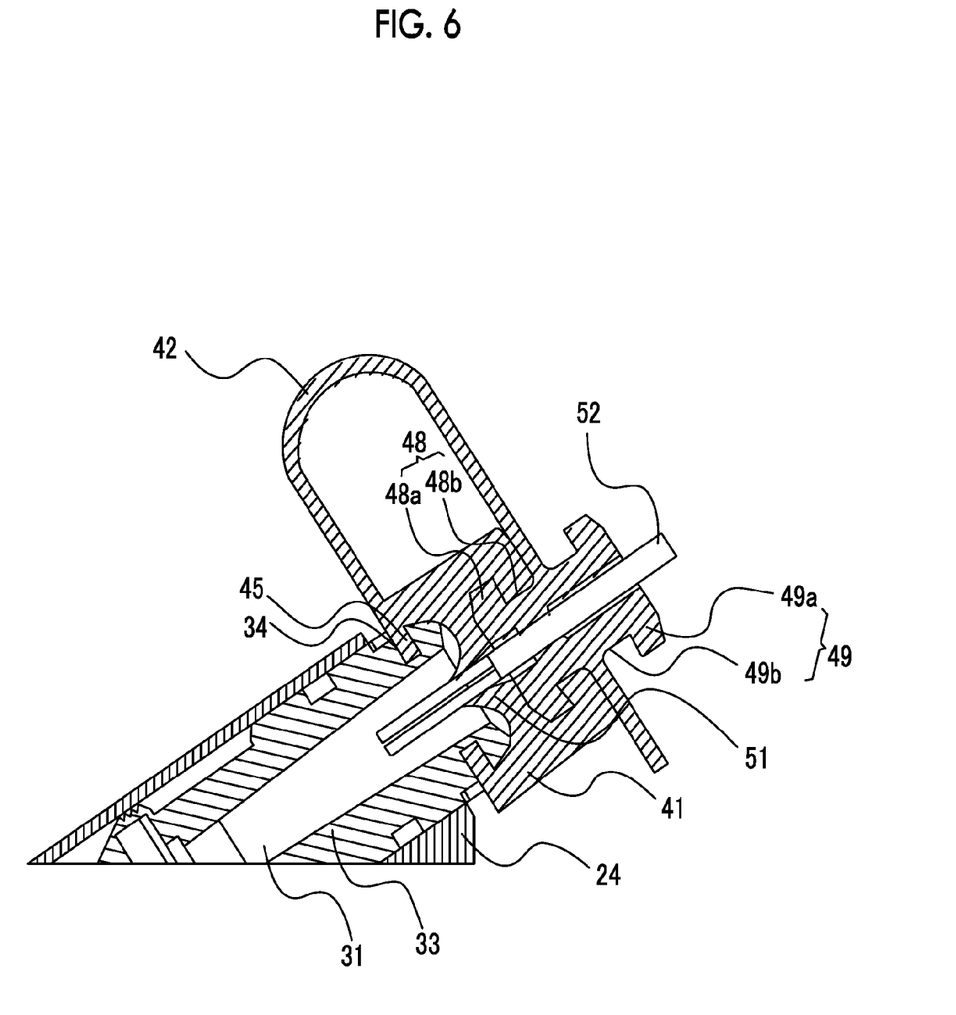
FIG. 6 is a cross-sectional view of a forceps plug when inserting a treatment instrument to a treatment instrument insertion channel.

If the treatment instrument 52 is inserted to the treatment instrument insertion channel 31, as illustrated in FIG. 6, the slit 50 is flexibly pressed to be open by a shaft of the treatment instrument 52. The treatment instrument 52 is guided into the subject by the rigid distal end 27 of the endoscope and thereby various treatments may be possible. In addition, when pulling out and removing the treatment instrument 52, the slit 50 is closed and thereby airtightness inside the treatment instrument insertion channel 31 may be maintained.

Figure 7:
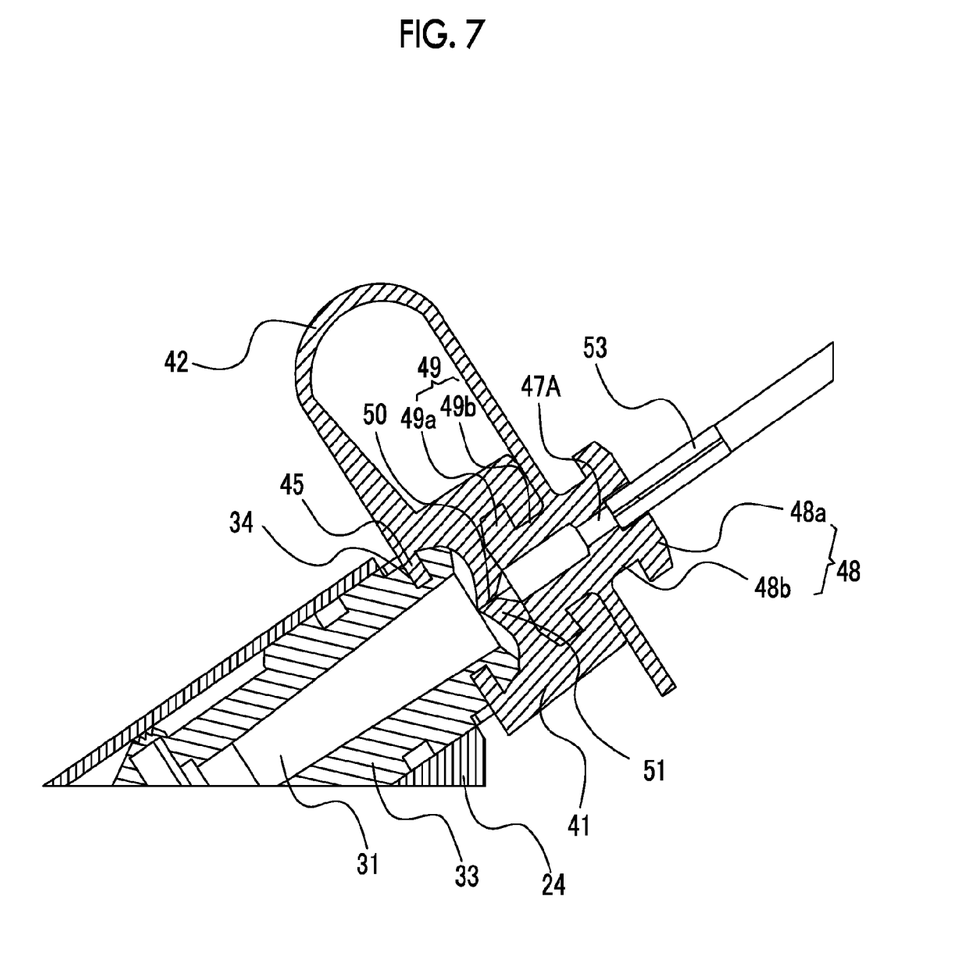
FIG. 7 is a cross-sectional view of a forceps plug when installing a second installation portion at a lid insertion portion.

FIG. 7 is a cross-sectional view of the forceps plug 40 when the second installation portion 49 of the lid 43 is installed at the lid insertion portion 46 of the main body 41. As illustrated in FIG. 7, when the second installation portion 49 of the lid 43 is installed at the lid insertion portion 46 of the main body 41, the outer diameter d4 of the second fitting portion 49b is small, the outer diameter d2 of the second insertion portion 49a is small, or both of the outer diameter d4 of the second fitting portion 49b and the outer diameter d2 of the second insertion portion 49a are small. Accordingly, the first installation portion 48 and the second installation portion 49 are not pressed by the outside main body 41 and the insertion channel 47A inside the first installation portion 48 may be unchanged compared to before the second installation portion 49 is installed at the lid insertion portion 46. Therefore, a bigger treatment instrument 53 than the treatment instrument 52 illustrated in FIG. 5 may be inserted to the insertion channel 47 of the lid 43. Herein, that the insertion channel 47A is unchanged does not mean that the diameter of the insertion channel 47A is unchanged even in a case of changes over time, or the application of an unexpected external force or the like to the first installation portion 48, that is, does not include that the diameter is unchanged.

According to the endoscope forceps plug of the present embodiment as described above, if an attachment direction of a lid member is changed, a portion of the treatment instrument insertion channel becomes slender (diameter of a portion of the treatment instrument insertion channel becomes small) or is changed in one side attachment direction and the portion of the treatment instrument insertion channel does not become slender or is not changed in the other side attachment direction. Therefore, plural kinds of treatment instruments are properly used such that prevention of liquid leakage and a reasonable insertion resistance of the forceps may be compatible when inserting the treatment instrument.

Hitherto, preferable embodiments of the present invention are described with reference to the accompanying drawings. However, the present invention is not limited to the specific embodiments thereof. It is obvious to those skilled in the art that various changes or modifications of the example are conceivable and obtainable within the scope of technical spirit disclosed in claims. Therefore, it is understood that all changes and modifications thereof are naturally included in the technical scope of the present invention.

For example, in the above-described embodiments, a case where the lid 43 is a flexible connection portion having flexibility and is connected to the main body 41 by the band-like portion 42 is described. However, the application of the present invention is not limited to the case. In the same manner, for example, when the second installation portion 49 of the lid 43 is installed at the lid insertion portion 46 of the main body 41, the connection portion of the band-like portion 42 and the main body 41 may be rotated, the band-like portion 42 may have the connection portion of a structure without being twisted and the connection portion may be formed from a string or the like.

What is claimed is:

1. An endoscope forceps plug that is used by being installed at a metal opening which communicates with a treatment instrument insertion channel provided at an endoscope so as to insert a treatment instrument, the endoscope forceps plug comprising:
    a main body that has an installation portion which is formed of an elastic material, having a cylinder shape and installed at the metal opening at one end side, and a lid insertion portion which cylindrically protrudes to the other end side and has a hole for inserting a lid; and
    the lid that is connected to the main body by a flexible connection portion having flexibility, that is formed of an elastic material, that has a tube shape with a cylindrical insertion channel inside into which the treatment instrument is inserted, and that, at both sides where both ends of the cylindrical insertion channel are respectively open, has first installation portion and second installation portion with different external shapes to each other which are installed being selectively inserted to the lid insertion portion,
    wherein the first installation portion has a larger external shape than the second installation portion, the external shape of the first installation portion and the second installation portion are slightly larger than the hole shape of the lid insertion portion such that the first installation portion and the second installation portion are elastically deformed and installed in the lid insertion portion, at least a portion of a diameter of the cylindrical insertion channel inside the first installation portion decreases in a case of installing the first installation portion to the lid insertion portion, and the diameter of the cylindrical insertion channel inside the first installation portion is unchanged in a case of installing the second installation portion to the lid insertion portion;
    wherein the first installation portion includes a first insertion portion which is inserted to a back side of the lid insertion portion, at a front part in an insertion direction to the lid insertion portion, and the second installation portion includes a second insertion portion which is inserted to the back side of the lid insertion portion, at the front part of the insertion direction to the lid insertion portion;
    wherein the first installation portion includes a first fitting portion which is fitted to an upper part of the lid insertion portion, at a rear part in the insertion direction to the lid insertion portion, and the second installation portion includes a second fitting portion which is fitted to the upper part of the lid insertion portion, at the rear part in the insertion direction to the lid insertion portion;
    wherein a diameter of the cylindrical insertion channel inside the first fitting portion at any position is less than a diameter of the cylindrical insertion channel inside the first insertion portion and a diameter of the cylindrical insertion channel inside the second installation portion.

2. The endoscope forceps plug according to claim 1, wherein the main body has a slit at a center portion of the main body, and the center portion of the main body is closed by a normally closed pit membrane which is open in a state of inserting the treatment instrument.

3. The endoscope forceps plug according to claim 2, wherein the first fitting portion has a larger outer diameter than the second fitting portion, in a state where the first and second insertion portions have the same outer diameter.

4. The endoscope forceps plug according to claim 2, wherein the first insertion portion has a larger outer diameter than the second insertion portion, in a state where the first and second fitting portions have the same outer diameter.

5. The endoscope forceps plug according to claim 2, wherein the first insertion portion has a larger outer diameter than the second insertion portion and the first fitting portion has a larger outer diameter than the second fitting portion, in a state where the first insertion portion and the second insertion portion have different outer diameters and the first and the second fitting portions have different outer diameters.

6. The endoscope forceps plug according to claim 2, wherein the installation portion of the main body has an elastic protrusion that protrudes on an inner peripheral surface and the elastic protrusion is detachably fitted into a forceps plug attachment groove which is formed on an outer peripheral surface of the metal opening.

7. The endoscope forceps plug according to claim 2, wherein a band-like portion has respective indications corresponding to inner diameters of different insertion channels on a surface of the first insertion portion side and a surface of the second insertion portion side.

8. The endoscope forceps plug according to claim 1, wherein the first fitting portion has a larger outer diameter than the second fitting portion, in a state where the first and second insertion portions have the same outer diameter.

9. The endoscope forceps plug according to claim 1, wherein the first insertion portion has a larger outer diameter than the second insertion portion, in a state where the first and second fitting portions have the same outer diameter.

10. The endoscope forceps plug according to claim 1, wherein the first insertion portion has a larger outer diameter than the second insertion portion and the first fitting portion has a larger outer diameter than the second fitting portion, in a state where the first insertion portion and the second insertion portion have different outer diameters and the first and the second fitting portions have different outer diameters.

11. The endoscope forceps plug according to claim 1, wherein the installation portion of the main body has an elastic protrusion that protrudes on an inner peripheral surface and the elastic protrusion is detachably fitted into a forceps plug attachment groove which is formed on an outer peripheral surface of the metal opening.

12. The endoscope forceps plug according to claim 1, wherein a band-like portion has respective indications corresponding to inner diameters of different insertion channels on a surface of the first insertion portion side and a surface of the second insertion portion side.

* * * * *